(12) United States Patent
McDaniel et al.

(10) Patent No.: US 9,173,693 B2
(45) Date of Patent: Nov. 3, 2015

(54) APPARATUS AND METHOD FOR STERNAL CLOSURE

(71) Applicants: Wayne C. McDaniel, Columbia, MO (US); Joseph T. Walls, Columbia, MO (US); Janet L. Rettenmaier, Columbia, MO (US)

(72) Inventors: Wayne C. McDaniel, Columbia, MO (US); Joseph T. Walls, Columbia, MO (US); Janet L. Rettenmaier, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 168 days.

(21) Appl. No.: 14/031,670

(22) Filed: Sep. 19, 2013

(65) Prior Publication Data

US 2014/0081340 A1    Mar. 20, 2014

Related U.S. Application Data

(60) Provisional application No. 61/744,156, filed on Sep. 19, 2012.

(51) Int. Cl.
| | |
|---|---|
| *A61B 17/86* | (2006.01) |
| *A61B 17/88* | (2006.01) |
| *A61B 17/70* | (2006.01) |
| *A61B 17/84* | (2006.01) |
| *A61B 17/72* | (2006.01) |
| *F16B 12/24* | (2006.01) |
| *A61B 17/80* | (2006.01) |
| *A61B 17/82* | (2006.01) |

(52) U.S. Cl.
CPC ......... *A61B 17/8685* (2013.01); *A61B 17/7098* (2013.01); *A61B 17/844* (2013.01); *A61B 17/864* (2013.01); *A61B 17/8811* (2013.01); *A61B 17/7225* (2013.01); *A61B 17/8076* (2013.01); *A61B 17/823* (2013.01); *A61B 17/842* (2013.01); *A61B 17/846* (2013.01); *A61B 17/8635* (2013.01); *F16B 12/24* (2013.01)

(58) Field of Classification Search
CPC ........... A61B 17/8685; A61B 17/8076; A61B 17/7225; F16B 12/24
See application file for complete search history.

(56) References Cited

U.S. PATENT DOCUMENTS 4,858,601 A * 8/1989 Glisson ........................ 606/916

* cited by examiner

*Primary Examiner* — Andrew Yang
(74) *Attorney, Agent, or Firm* — Polster Lieder

(57) ABSTRACT

The present disclosure provides a sternal closure fixation device. The fixation device includes a first sternum implant disposable within an interior cavity of a first half of a severed sternum such that the first implant contacts opposing anterior and posterior faces of the cavity. The fixation device additionally includes, a second sternum implant disposable within an interior cavity of a second half of a severed sternum such that the second implant contacts opposing anterior and posterior faces of the cavity. Furthermore, the fixation device includes a rigid fixation pin sized and structured to be disposed within an internal bore of the first implant and within an internal bore of the second implant, whereby when the first and second halves of the severed sternum are joined together, the first and second halves of the sternum are prevented from shear movement in any direction relative to each other.

14 Claims, 5 Drawing Sheets

APPARATUS AND METHOD FOR STERNAL CLOSURE

CROSS-REFERENCE TO RELATED APPLICATIONS

This application claims the benefit of U.S. Provisional Application No. 61/744,156, filed on Sep. 19, 2012. The disclosure of the above application is incorporated herein by reference in its entirety.

The present teachings relate to a surgical device for sternal closure and method of use thereof.

BACKGROUND

The statements in this section merely provide background information related to the present disclosure and may not constitute prior art.

A median sternotomy, or cutting through the breastbone, is one of the most common surgical procedures performed. When first described, the recommended method of closure was to insert steel wires around the severed sternum and twist the ends to hold the two sternal halves tightly together. Today, this method, commonly known as the Cerclage wire method, is still the most common method of sternal closure. However, many problems with this method have been reported. For example, wires have been known to loosen (or even break) over time as the patient returns to everyday activities after surgery. Additionally, it is known that, although Cerclage wires are generally sufficient to maintain the opposing faces of the severed sternum in contact and prevent the severed sternum from separating, i.e., pulling apart such that there is a gap between the opposing faces, Cerclage wires generally do not prevent shear movement of the opposing halves relative to each other along the plane of the osteotomy. Furthermore, closing a median sternotomy in an osteoporotic patient, wherein their bone is resorbed, yielding thin, soft bone, is particularly challenging, because the sternum can be very pliable and the tightening of the Cerclage wires can actually crush the sternum.

Movement at the osteotomy line disrupts revascularization and slows healing. If there are gaps or movement along the osteotomy line, the bone healing can be greatly incumbered. Hence, to achieve optimal healing of the severed sternum, the relative movement of the two sternal halves, in every direction (longitudinal shear, horizontal separation, in-and-out shear, etc.) needs to be prevented, or minimized. Cerclage wires generally prevent horizontal separation (if they do not loosen with stress), however, they do not prevent shear movement between the sternal halves.

Several methods have been attempted to better hold the two sternal halves together, and improve the healing process of the sternum, but none of these has gained wide-spread acceptance in practice.

SUMMARY

The present disclosure provides a device for sternal closure with improved security on holding the two sternal halves together after a median sternotomy. The device comprises a pair of bone implants, which can be made of inert materials, that are inserted into each of the sternum halves perpendicular to the cut surface. The inserts are disposed within the respective sternum halves by either screwing or pressing the inserts into the bone marrow, i.e., into the cancellous bone, with each implant making contact with one or both of the respective sternal cortices. Each pair of inserts are implanted in directly opposing positions within the two opposing sternal halves such that a pin can bridge each respective pair of inserts and be pushed into the opposing inserts as the two halves of the sternum are apposed and pulled together. Subsequently, Cerclage wires can be used to apply compression to the sternum at the osteotomy site and hold the two sternal halves together while the inserts and pins prevent shear movement of the sternal halves.

Further areas of applicability of the present teachings will become apparent from the description provided herein. It should be understood that the description and specific examples are intended for purposes of illustration only and are not intended to limit the scope of the present teachings.

DRAWINGS

The drawings described herein are for illustration purposes only and are not intended to limit the scope of the present teachings in any way.

Corresponding reference numerals indicate corresponding parts throughout the several views of drawings.

DETAILED DESCRIPTION

Figure 1:
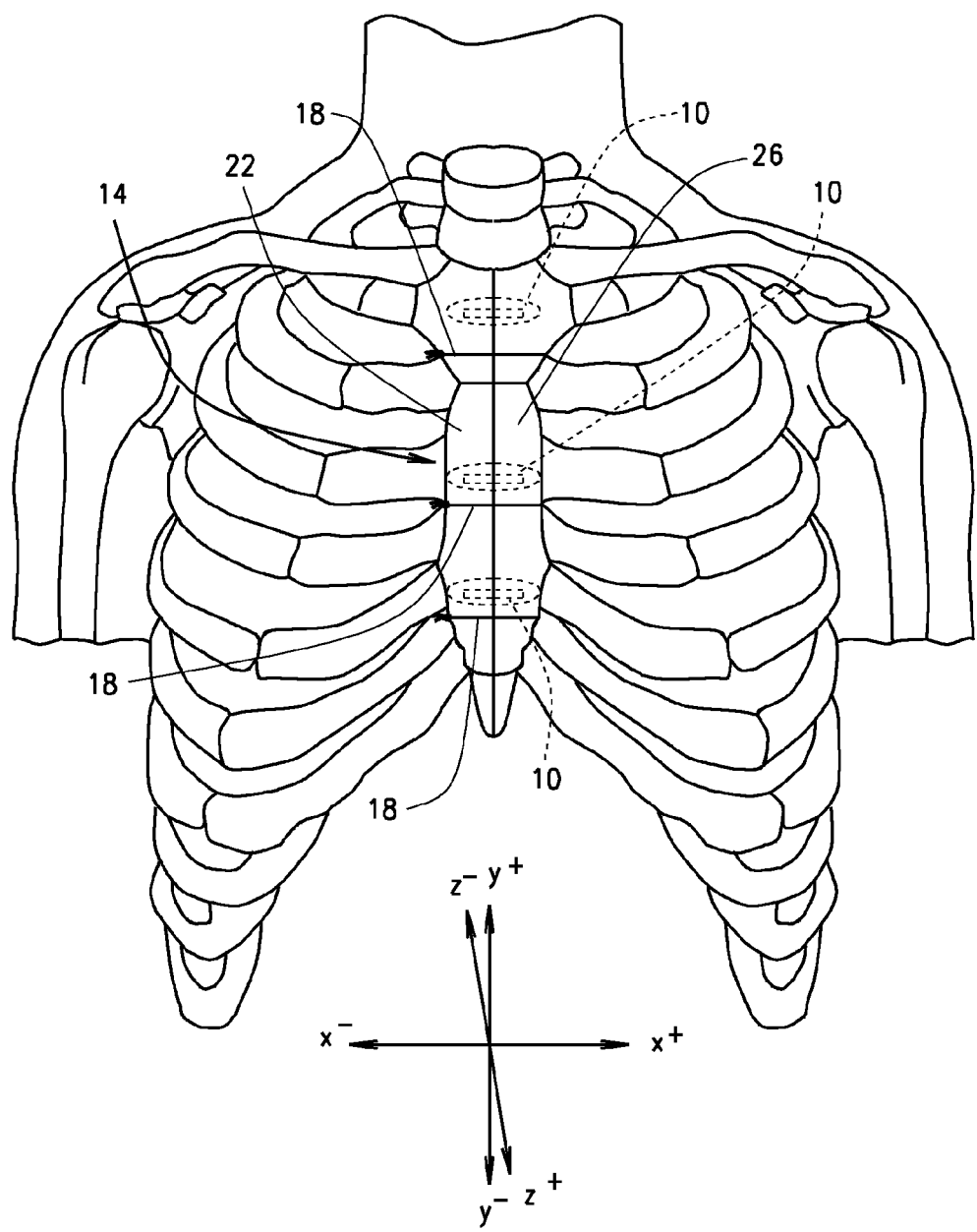
FIG. 1 is a schematic of a sternum that has been closed, after a median sternotomy, utilizing at least one sternal closure fixation device, in accordance with various embodiments of the present disclosure.
Figure 2:
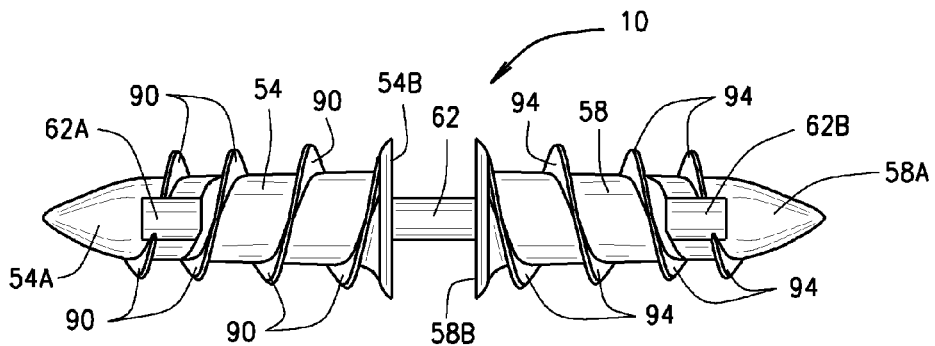
FIG. 2, is a side view of the sternal closure fixation device, shown in FIG. 1, in accordance with various embodiments of the present disclosure.
Figure 3:
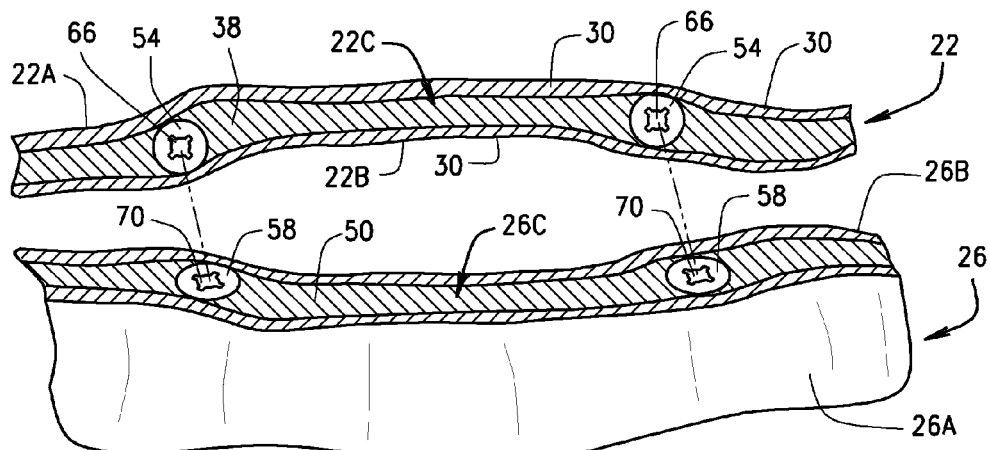
FIG. 3 is a sectional view of a portion of a severed sternum having implants of the sternal closure fixation device shown in FIG. 1 disposed within the cancellous bone that fills the interior cavity of the cortical bone of each half of the severed sternum, in accordance with various embodiments of the present disclosure.
Figure 4:
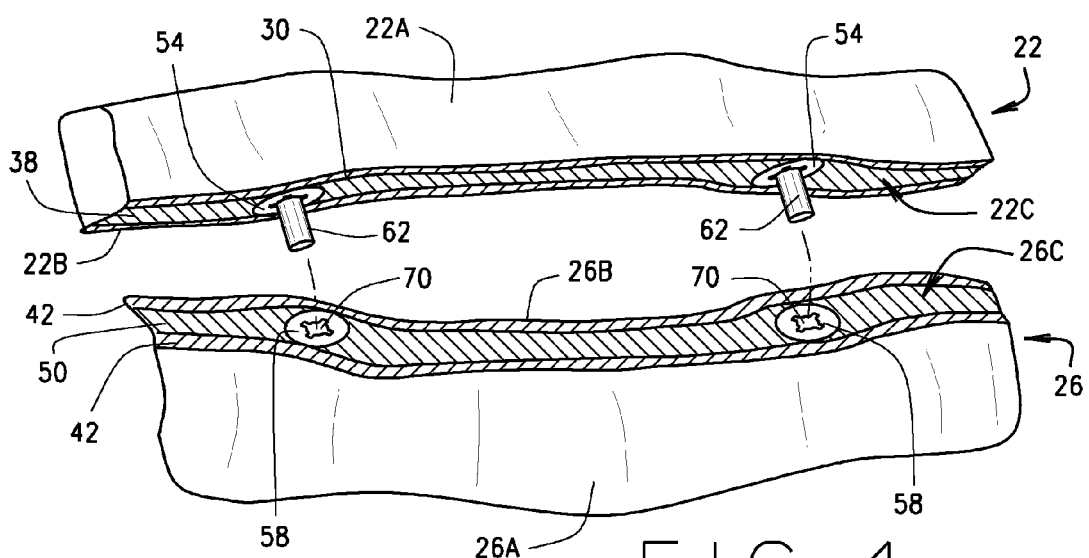
FIG. 4 is a sectional view of the portion of the severed sternum shown in FIG. 3 having a rigid fixation pin of the sternal closure fixation device shown in FIG. 1 disposed within the opposing implants, in accordance with various embodiments of the present disclosure.

The following description is merely exemplary in nature and is in no way intended to limit the present teachings, application, or uses. Throughout this specification, like reference numerals will be used to refer to like elements.

Referring now to FIG. 1, the present disclosure provides a sternal closure fixation device 10 for use when closing, or repairing, a sternum 14 that has been severed during a sternotomy, i.e., joining the opposing halves of the severed sternum 14. More specifically, the fixation device 10 is structured and operable to be implanted within the severed sternum 14, i.e., disposed within the cancellous bone tissue of the severed sternum 14, and prevent sheer movement of sternum halves relative to each other, i.e., movement in the $Y^{+/-}$ and/or $Z^{+/-}$ directions relative to each other, once the sternum is closed.

As used herein, the phrases "closing the sternum" or "to close the sternum" will be understood to mean bringing the two halves of the severed sternum back together and securing them together, and the phase "closed sternum" will be understood to mean once the two halves of the sternum have been brought back together and secured together. The two halves of the severed sternum 14 can be secured together using a securing device 18 that can be any suitable securing device, apparatus or system, such as a wire wrapped around the sternum halves and twisted at the ends (commonly referred to as the Cerclage wire technique), a metal band bent around the joined sternum halves, a bio-compatible or absorbable plastic tie-wrap wrapped around the sternum halves, etc.

Referring now to FIGS. 1 through 6, during a sternotomy the sternum 14 is severed to separate the sternum 14 into a first half 22 and a second half 26. The first and second halves 22 and 26 each respectively comprise an external anterior face 22A and 26A, an external posterior face 22B and 26B, and a severance face 22C and 26C created upon severance of the sternum 14. As is well known, the sternum 14 is comprised of soft cancellous bone tissue surrounded by hard cortical bone tissue. Hence, the first half 22 comprises a cortical bone shell 30 that defines an interior cavity 34 (best shown in FIG. 5) that is filled with cancellous bone tissue 38, and the second half 26 comprises a cortical bone shell 42 that defines an interior cavity 46 (best shown in FIG. 5) that is filled with cancellous bone tissue 50. It should be noted that, prior to severance of the sternum 14 and subsequent to closure of the severed sternum 14, the first and second cortical bone shells 30 and 42 comprehensively comprise the entire cortical shell of the sternum 14, the first and second cavities 34 and 46 comprehensively comprise the entire interior cavity of the sternum 14, and the first and second cancellous bone tissue 38 and 50 comprehensively comprise the entire cancellous bone tissue that fills the interior cavity of the sternum 14.

In various implementations, as exemplarily illustrated in FIG. 1, one or more of fixation devices 10 can be utilized to close the sternum 14. However, for clarity and simplicity, only a single fixation device 10 will be described hereafter. The fixation device 10 comprises a first implant 54, a second implant 58 and a rigid fixation pin 62. The first implant 54 is sized and structured to be disposed within the interior cavity 38 of the cortical bone shell 30 of the first half 22 of the severed sternum 14. The second implant 58 is sized and structured to be disposed within the interior cavity 46 of the cortical bone shell 42 of the second half 26 of the severed sternum 14. And, the fixation pin 62 is sized and structured to frictionally fit within an internal bore 66 of the first implant 54 and an internal bore 70 of the second implant 58.

More specifically, the first implant 54 is structured and operable to be inserted directly into the first half cancellous tissue 38, via the first half severance face 22C, and disposed within the first half interior cavity 34, via screwing, pushing, impacting, or any other suitable means, such that the first implant 54 contacts at least one of an anterior face 74A and a posterior face 74B of an interior wall 74 of the first half cortical bone shell 30. Similarly, the second implant 58 is structured and operable to be inserted directly into the second half cancellous tissue 50, via the second half severance face 26C, and disposed within the second half interior cavity 46, via screwing, pushing, impacting, or any other suitable means, such that the second implant 58 contacts at least one of an anterior face 78A and a posterior face 78B of an interior wall 78 of the second half cortical bone shell 42. Additionally, a first half 62A of the fixation pin 62 is sized and structured to fit snugly within the first implant internal bore 66 and a second half 62B of the fixation pin 62 is sized and structured to fit snugly within the second implant internal bore 70. That is, the fixation pin 62 is sized and structured to fit within the first and second implant bores 66 and 70 such that the outer surface of the fixation pin is in firm contact with in inner surface of the respective bores 66 and 70 such that there is no play or space between the pin outer surface and the bore inner surfaces and the first and second implants are rigidly connected to the fixation pin 62 when the pin is disposed within the respective internal bores 66 and 70.

Figure 6:
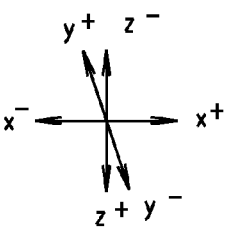
FIG. 6 is a cross-sectional view of the two halves of the severed sternum, having the sternal closure fixation device disposed within the respective cortical bone interior cavities as shown in FIG. 5, joined together using a tie wire, in accordance with various embodiments of the present disclosure.
Figure 6:
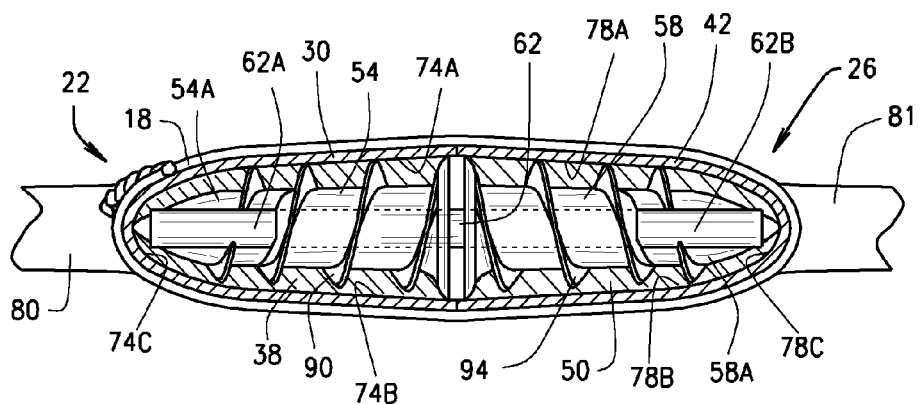

Therefore, as exemplarily illustrated in FIG. 6, when the first and second halves 22 and 26 of the severed sternum 14 are joined together, i.e., the sternum is closed, to bring the first and second severance faces 22C and 26C into contact with each other, with at least one fixation device 10 implanted within the sternum 14 as described herein, the fixation device 10 prevents the first and second halves 22 and 26 of the sternum 14 from shear movement in any direction along a plane of the contacting first and second severance faces 22C and 26C. That is, the rigid connection of the fixation pin 62 within the internal bores 66 and 70 of the first and second implants 54 and 58 will prevent shear movement of the first and second halves 22 and 26, relative to each other. More specifically, the first and second halves 22 and 26 are prevented from movement in the $Y^{+/-}$ and $Z^{+/-}$ directions. The $Y^{+/-}$ directions are defined herein as anterior and posterior movement (with respect to the patient's chest) of the severed sternum first and second halves 22 and 26 relative to each other, and the $Z^{+/-}$ directions are defined herein as longitudinal movement (with respect to a longitudinal axis of the patient) of the severed sternum first and second halves 22 and 26 relative to each other. Lateral movement, or separation, of the severed sternum first and second halves 22 and 26, in the $X^{+/-}$ directions is prevented by the one or more securing devices 18.

Figure 5:
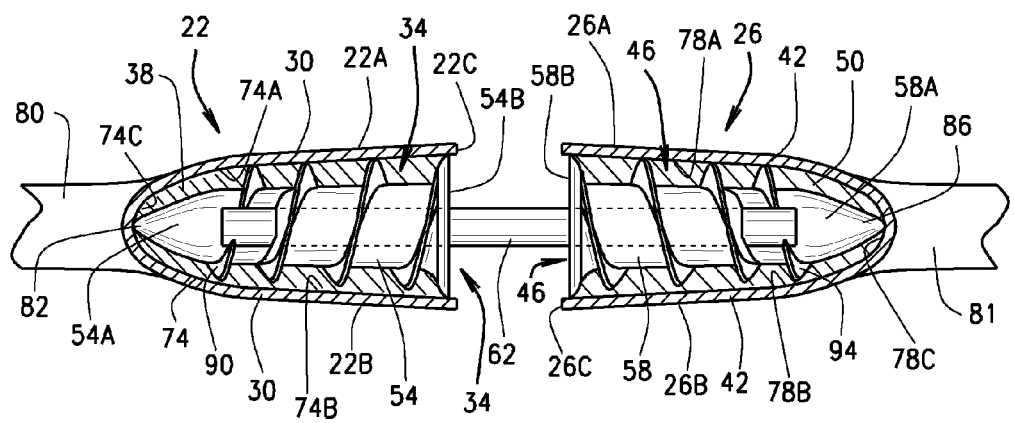
FIG. 5 is a cross-sectional view of a severed sternum having the sternal closure fixation device shown in FIG. 2 disposed within the interior cavity of the sternum cortical bone of each half of the severed sternum, in accordance with various embodiments of the present disclosure.
Figure 7:
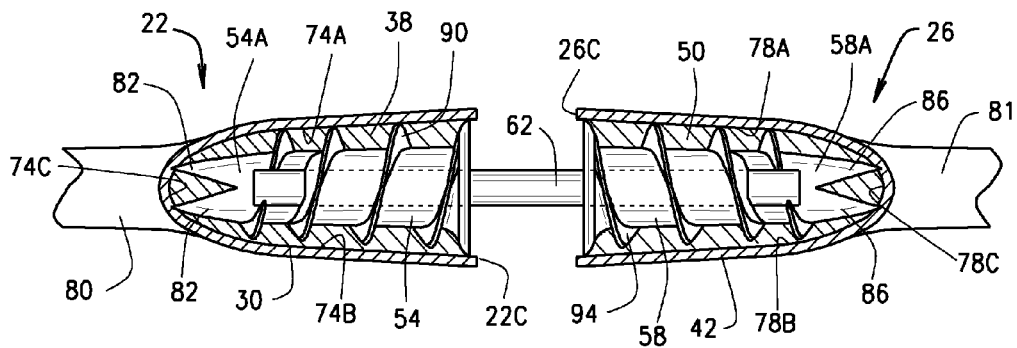
FIG. 7 is a cross-sectional view of a severed sternum having the sternal closure fixation device shown in FIG. 1 disposed within the interior cavity of the sternum cortical bone of each half of the severed sternum, in accordance with various other embodiments of the present disclosure.

Referring now to FIGS. 5, 6 and 7, in various embodiments, the first and second implants 54 and 58 are sized and structured such that, in addition to contacting at least one of the anterior faces 74A and 78A and the posterior faces 74B and 78B of an interior walls 74 and 78, a distal end 54A of the first implant 54 contacts a costal margin face 74C of the interior wall 74 of the first half cortical bone shell 30, and a distal end 58A of the second implant 58 contacts a costal margin face 78C of the interior wall 78 of the second half cortical bone shell 42, thereby adding additional stability and fixation of the implants 54 and 58 within the respective sternum halves 22 and 26. As will be easily and readily understood by one skilled in the art, the greater the stability and fixation of the implants 54 and 58 within the respective sternum halves 22 and 26 is, the less the implants 54 and 58 will move within the respective first and second sternum cavities 34 and 46, and hence, the greater the fixation device 10 will function to prevent sheer movement of the severed sternum first and second halves 22 and 26 in the $Y^{+/-}$ and $Z^{+/-}$ directions, relative to each other, once the sternum 14 is closed, as described herein.

For example, in various embodiments, the distal ends 54A and 58A can comprise one or more tines 82 and 86, respectively, whereby, when the first and second implants 54 and 58 are disposed within the respective interior cavities 34 and 46, the one or more tines 82 and 86 contact the respective costal margin face 74C and 78C, thereby adding additional stability and fixation of the implants 54 and 58 within the respective sternum halves 22 and 26. In various other embodiments, the distal end tines 82 and 86 can be shaped and structured to penetrate, embed into, or cut into the respective costal margin faces 74C and 78C, thereby adding additional stability and fixation of the implants 54 and 58 within the respective sternum halves 22 and 26. For example, the distal end tines 82 and 86 can have a spiked, pointed or sharpened tip that will penetrate, embed into, or cut into the respective costal margin faces 74C and 78C.

Such embodiments, wherein the distal ends 54A and 58A of the first and second implant 54 and 58 contact the respective costal margin faces 74C and 78C are very applicable for osteoporotic patients where the cortical bone is soft and fragile. More particularly, it is well known, that the costal margins of the respective first and second sternum halves 22 and 26 are connected to the ribs via cartilage 80 and 81, respectively. Hence, there is greater, denser, more rigid skeletal structure along the costal margins of the respective sternum halves 22 and 26. Thus, disposing the first and second implants 54 and 56 within the respective cavities 34 and 46 such that distal ends 54A and 58A contact, penetrate, embed into, or cut into the respective costal margin faces 74C and 78C not only adds stability and fixation of the implants 54 and 56 within the respective first and second sternum halves 22 and 26, but also can prevent the first and second sternum halves 22 and 26 from 'accordioning', i.e., collapsing or scrunching up when the securing device 18 is put in place to secure the first and second halves together, as described herein.

Referring now to FIGS. 2, 5, 6 and 7, in various embodiments, the first and second implants 54 and 58 can each comprise an external helical thread 90 and 94, respectively. In such embodiments, the helical threads 90 and 94 are structured and operable to enable the respective implants 54 and 58 to be screwed, or threaded, into the cancellous bone 38 and 50 that fills the interior cavities 34 and 46 of the cortical bone shells 30 and 42 of the respective halves 22 and 26 of the severed sternum 14. Additionally, in such embodiments, the helical threads 90 and 94 can be further structured and operable to provide a plurality of lines of contact between the implant helical threads 90 and 94 and the anterior and posterior faces 74A, 74B, 78A and 78B of the respective cortical bone interior walls 74 and 78, thereby adding additional stability and fixation of the implants 54 and 58 within the respective sternum halves 22 and 26.

Figure 8:
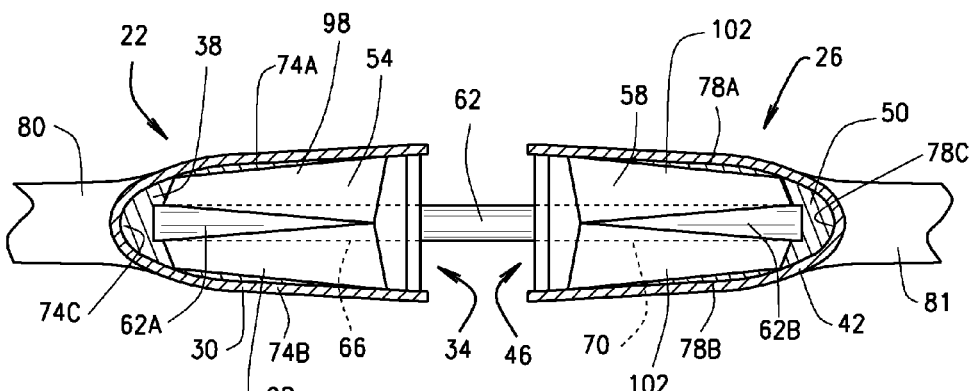
FIG. 8 is a cross-sectional view of a severed sternum having the sternal closure fixation device shown in FIG. 1 disposed within the interior cavity of the sternum cortical bone of each half of the severed sternum, in accordance with various yet other embodiments of the present disclosure.

Referring now to FIG. 8, in various embodiments, the first and second implants 54 and 58 are structured to comprise at least two legs 98 and 102, respectively, that define the respective internal bores 66 and 70. In such embodiments, each internal bore 66 and 70 is tapered toward the distal end. Therefore, when the fixation pin 62 is disposed within the internal bores 66 and 70, the legs 98 and 102 of the respective first and second implant 54 and 58 will be forced radially outward. That is, once the first and second implants 54 and 58 have been implanted within respective first and second cavities 34 and 46, as the fixation pin 62 is pushed into the tapered bores 66 and 70 of the respective implants 54 and 58, the fixation pin 62 will force the legs 98 and 102 radially outward toward the opposing anterior and posterior faces 74A, 74B, 78A and 78B of the respective cortical bone interior walls 74 and 78 such that the legs 98 and 102 of the respective implants 54 and 58 firmly contact the respective opposing anterior and posterior faces 74A, 74B, 78A and 78B. Accordingly, the implants 54 and 58 will be stably and fixedly secured within the respective sternum halves 22 and 26.

Figure 9:
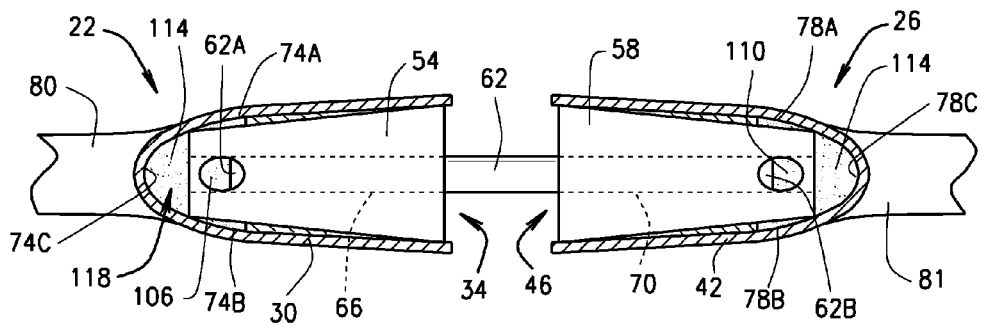
FIG. 9 is a cross-sectional view of a severed sternum having the sternal closure fixation device shown in FIG. 1 disposed within the interior cavity of the sternum cortical bone of each half of the severed sternum, in accordance with various still other embodiments of the present disclosure.

Referring now to FIG. 9, in various embodiments, the first and second implants 54 and 58 each comprise at least one extrusion bore 106 and 110, respectively. The extrusion bores 106 and 110 extend through the distal end portions 54A and 58A of the respective implants 54 and 58 and intersect the respective internal bores 66 and 70. In such embodiments, a bone filler 114, e.g., cement, or glue, can be pushed through the internal bores 66 and 70 and be extruded from the respective extrusion bores 106 and 110 into costal margin end portions 118 and 122 of the respective cortical bone cavities 34 and 46. Consequently, the extruded bone filler 114 will provide a large area of contact between the anterior, posterior and costal margin faces 74A, 74B, 74C, 78A, 78B and 78C of the respective cortical bone cavities 34 and 46, thereby stably and fixedly securing the first and second implants 54 and 58 within the respective sternum halves 22 and 26.

Figure 10:
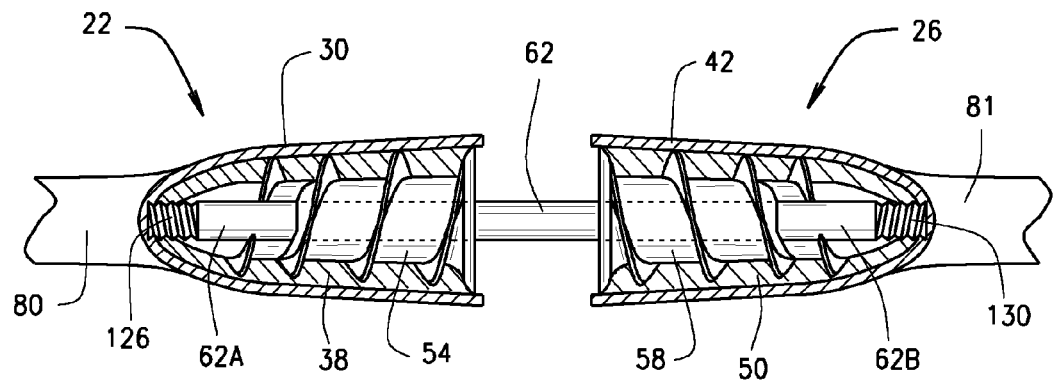
FIG. 10 is a cross-sectional view of a severed sternum having the sternal closure fixation device shown in FIG. 1 disposed within the interior cavity of the sternum cortical bone of each half of the severed sternum, in accordance with various still yet other embodiments of the present disclosure.

Referring now to FIG. 10, in various embodiments, the distal end of the fixation pin first half 62A includes threads 126 formed therein, and the distal end of the fixation pin second half 62B includes threads 130 formed therein. In such embodiments, upon closure of the sternum 14, utilizing the first and second implants 54 and 58 as described above, the distal ends of first and second halves 62A and 62B of the fixation pin 62 can be threaded into the costal margin portion of the respective first and second halves 22 and 26 of the severed sternum 14. Threading the distal ends of first and second halves 62A and 62B of the fixation pin 62 into the costal margin portion of the respective first and second halves 22 and 26 of the severed sternum 14 will aid the securing device 18 in retaining the first and second severance faces 22C and 26C in contact with each other and prevent separation of the severed sternum halves 22 and 26 in the $X^{+/-}$ direction, and will additionally provide additional stability and fixation of the first and second implants 54 and 58 within the respective sternum halves 22 and 26.

Figure 11:
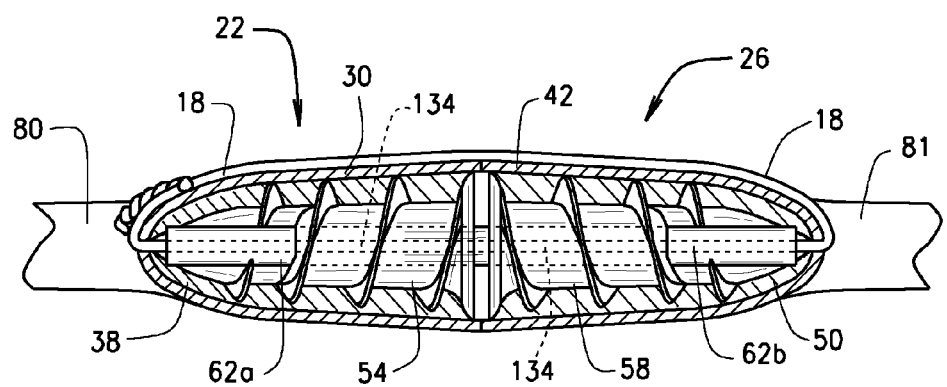
FIG. 11 is a cross-sectional view of a severed sternum having the sternal closure fixation device shown in FIG. 1 disposed within the interior cavity of the sternum cortical bone of each half of the severed sternum, in accordance with various yet other embodiments of the present disclosure.

Referring now to FIG. 11, in various embodiments, the fixation pin 62 comprises an internal lumen 134 structured and operable to receive a tie wire securing device 18. As described above, the securing device 18, in this instance the tie wire, is used to bring the first and second severance faces 22C and 26C, respectively, into contact with each other to join the first and second halves 22 and 26 of the severed sternum 14, i.e., to close the sternum 14. In such embodiments small holes would be made in the costal margins of the first and second halves 22 and 26 of the severed sternum 14, whereby the tie wire can be inserted through one of the costal margin holes, pushed through the internal lumen 134 of the fixation pin 62 and out the opposing costal margin hole, whereafter the ends of the tie wire can be twisted to securely retain the first and second severance faces 22C and 26C in contact with each other. Additionally, having the tie wire securing device 18 inserted through the costal margin holes and the fixation device internal lumen 134 will provide additional stability and fixation of the first and second implants 54 and 58 within the respective sternum halves 22 and 26.

Referring now to FIGS. 1 through 11, use of the fixation device 10 can be effectuated by first disposing the first implant 54 within the interior cavity 34 of the cortical bone shell 30 of the first half 22 of a severed sternum 14. Particularly, the first implant 54 is disposed within the cancellous bone tissue 38 filling interior cavity 34, and disposed such that the first implant 54 firmly contacts the opposing anterior and posterior faces 74A and 74B of the interior wall 74 of the first half cortical bone shell 30. In various implementations, in addition to the contact between the first implant 54 and the opposing anterior and posterior faces 74A and 74B, the distal end 54A of the first implant 54 firmly contacts, penetrates, embeds into, or cuts into the costal margin face 74C of the first half cortical bone interior wall 74. Additionally, the first implant 54 is disposed within the cancellous bone tissue 38 such that a proximal end 54B of the first implant 54 is substantially flush with, or slightly recessed within, the severance face 22C of the severed sternum first half 22.

Subsequently, the second implant 58 is disposed within the interior cavity 46 of the cortical bone shell 42 of the second half 26 of a severed sternum 14. Particularly, the second implant 58 is disposed within the cancellous bone tissue 50 filling interior cavity 46, and disposed such that the second implant 54 firmly contacts the opposing anterior and posterior faces 78A and 78B of the interior wall 78 of the second half cortical bone shell 42. In various implementations, in addition to the contact between the second implant 58 and the opposing anterior and posterior faces 78A and 78B, the distal end 58A of the second implant 58 firmly contacts, penetrates, embeds into, or cuts into the costal margin face 78C of the second half cortical bone interior wall 78. Additionally, the second implant 58 is disposed within the cancellous bone tissue 50 such that a proximal end 58B of the second implant 58 is substantially flush with, or slightly recessed within, the severance face 26C of the severed sternum second half 26.

Next, the distal end the first half 62A of the fixation pin 62 is inserted into the internal bore 66 of the first implant 54, and the distal end of the second half 62B of the fixation pin 62 is inserted into the internal bore 70 of the second implant 58. Thereafter, the first and second halves 22 and 26 of the severed sternum 14 are pulled together such that the first and second severance faces 22C and 26C are brought into contact with each other. This will push the first and second halves 62A and 62B of fixation pin 62 further within the internal bores 66 and 70 of the respective first and second implants 54 and 58. Subsequently, the first and second halves 22 and 26 of the severed sternum 14 are secured together using the securing device 18. Consequently, as described above, the securing device 18 will prevent that lateral separation, or movement in the $X^{+/-}$ directions, of the first and second sternum halves 22 and 26. And, importantly, the fixation device 10 will prevent shear movement of the first and second sternum halves 22 and 26, relative to each other, in any direction along a plane of the contacting first and second severance faces 22C and 26C. That is, the fixation device 10 will prevent shear movement of the first and second sternum halves 22 and 26 relative to each other in the $Y^{+/-}$ and $Z^{+/-}$ directions.

Prevention of shear movement of the first and second sternum halves 22 and 26 relative to each other in the $Y^{+/-}$ and $Z^{+/-}$ directions will dramatically increase the ability of the closed sternum 14 to heal and greatly reduce recovery time for the patient.

It is envisioned that the first and second implants 54 and 58 can be structured to have various sizes and/or shapes such that appropriately sized and/or shaped first and second implants 54 and 58 can be selected to match the size and/or shape of the respective sternum first and second halves 22 and 26.

Furthermore, it is envisioned that it will be advantageous to dispose at least one of the fixation devices 10 within the manubrium of the patient, because the manubrium is cartilaginous tissue and therefore a much stronger structure in which to implant the fixation device 10. In such embodiments, the first and second implants 54 and 58 can be made a material that is suitable for disposition within the more cartilaginous tissue of the manubrium.

Still further, although the first and second implants 54 and 58 are shown throughout the various figures as being generally cylindrical, it is envisioned that the first and second implants 54 and 58 can have any cross-sectional shape, e.g., square, rectangular, triangular, oval, etc.

Still further yet, it is envisioned that the first and second implants 54 and 58 and/or the fixation pin 62 can be constructed, or fabricated, of any suitable biocompatible material, and in various instances be constructed, or fabricated, of a material that will dissolve or be absorbed over time (i.e., after the sternum 14 has completely healed).

As described above, a particularly important application of the fixation device 10 is in osteoporotic bone. Frequently elderly patients will be afflicted by osteoporosis, wherein their bone is resorbed, yielding thin, soft bone. Closing a median sternotomy in an osteoporotic patient is particularly challenging, as the bone can be pliable. The use of the fixation device 10 in these patients would give a rigid internal frame to promote bone healing.

The description herein is merely exemplary in nature and, thus, variations that do not depart from the gist of that which is described are intended to be within the scope of the teachings. Such variations are not to be regarded as a departure from the spirit and scope of the teachings.

What is claimed is:

1. A sternal closure fixation device, said device comprising:
a first sternum implant sized and structured to be disposed within an interior cavity of a cortical bone of a first half of a severed sternum such that the first implant contacts at least opposing anterior and posterior faces of an interior wall of the first half cortical bone of the severed sternum first half, the severed sternum first half having a first severance face produced by severance of the sternum, the first implant comprising at least one pointed tine structured and operable to at least one of contact and penetrate a costal margin face of the interior wall of the cortical bone of the first half of the severed sternum when the first implant is disposed within the interior cavity of the first half of the severed sternum;
a second sternum implant sized and structured to be disposed within an interior cavity of a cortical bone of a second half of the severed sternum, opposing the first implant, such that the second implant contacts at least opposing anterior and posterior faces of an interior wall of the second half cortical bone of the severed sternum second half, the severed sternum second half having a second severance face produced by severance of the sternum, the second implant comprising at least one pointed tine structured and operable to at least one of contact and penetrate a costal margin face of the interior wall of the cortical bone of the second half of the severed sternum when the second implant is disposed within the interior cavity of the second half of the severed sternum; and a cylindrical rigid fixation pin having a constant diameter along a length thereof that is sized and structured to be disposed within an internal bore of the first implant and within an internal bore of the second implant, whereby when the first and second halves of the severed sternum are joined to bring the first and second severance faces into contact with each other, the first and second halves of the sternum are prevented from shear movement in any direction along a plane of the contacting first and second severance faces, wherein the first and second implants each comprise at least two legs that define the respective internal bore, and wherein each internal bore is tapered toward a distal end such that when the fixation pin is disposed within the internal bores the legs of each respective implant will be forced radially outward such that each respective implant firmly contacts the opposing faces of the interior wall of the respective cortical bone.

2. The device of claim 1, wherein the first and second implants are sized and structured to be disposed within an interior cavity of the cortical bone of the respective first and second half of the severed sternum such that the each implant contacts the opposing anterior and posterior faces of the interior wall of the cortical bone of the respective half and a costal margin face of the interior wall of the cortical bone of the respective half.

3. The device of claim 1, wherein the first and second implants each comprise an external helical thread structured and operable to screw the respective implant into cancellous bone that fills the interior cavity of the cortical bone of the respective half of the severed sternum.

4. The device of claim 1, wherein the first and second implants each comprise at least one extrusion bore extending through a distal end portion of the respective implant and intersecting the respective internal bore, such that a bone filler can be extruded from the respective extrusion bore and disposed within a costal margin end portion of the respective cortical bone.

5. The device of claim 1, wherein opposing distal ends of the fixation pin comprise threads such that each threaded distal end of the fixation pin can be threaded into the costal margin of the respective half of the severed sternum.

6. The device of claim 1, wherein the fixation pin comprises an internal lumen structured and operable to receive a tie wire used to bring the first and second severance faces into contact with each other and join the first and second halves of the severed sternum.

7. A method for sternal closure, said method comprising:
disposing a first implant of a sternal closure fixation device within an interior cavity of a cortical bone of a first half of a severed sternum such that the first implant contacts at least opposing anterior and posterior faces of an interior wall of the cortical bone of the severed sternum first half and a proximal end face of the first implant is substantially flush with a first severance face of the severed sternum first half produced by severance of the sternum;
disposing, substantially opposite the first implant, a second implant of the sternal closure device within an interior cavity of a cortical bone of a second half of the severed sternum, such that the second implant contacts at least opposing anterior and posterior faces of an interior wall of the cortical bone of the severed sternum second half and a proximal end face of the second implant is substantially flush with a second severance face of the severed sternum second half produced by severance of the sternum;
inserting a first distal end of a rigid fixation pin of the sternal closure fixation into an internal bore of the first implant;
inserting an opposing second distal end of the rigid fixation pin into an internal bore of the second implant;
pulling the first and second halves of the severed sternum together such that the first and second severance faces are brought into contact with each other and the fixation pin is pushed within each of the first and second implants; and
securing the first and second halves of the severed sternum together such that lateral separation of the first and second halves is prevented, whereafter the sternal closure fixation device prevents shear movement of the first and second halves in any direction along a plane of the contacting first and second severance faces.

8. The method of claim 7, wherein disposing the first and second implants comprises disposing the first and second implants within the interior cavity of the cortical bone of the respective first and second half of the severed sternum such that the each implant contacts the opposing faces of the interior wall of the respective cortical bone and a costal margin face of the interior wall of the respective cortical bone.

9. The method of claim 7, wherein disposing the first and second implants comprises screwing the respective implant into cancellous bone that fills the interior cavity of the cortical bone of the respective half of the severed sternum utilizing an external helical thread formed on an exterior of each of the first and second implants.

10. The method of claim 7, wherein disposing the first and second implants comprises disposing the first and second implants within the interior cavity of the cortical bone of the respective first and second half of the severed sternum such that the each implant contacts the opposing faces of the interior wall of the cortical bone and at least one tine formed at a distal end of the respective implant at least one of contacts and penetrates a costal margin face of the interior wall of the respective cortical bone.

11. The method of claim 7, wherein the first and second implants each comprise at least two legs that define the respective internal bore, and wherein each internal bore is tapered toward a distal end, and wherein pulling the first and second halves of the severed sternum together comprises pulling the first and second halves together such that the fixation pin is pushed within each of the tapered internal bores forcing the legs of each respective implant radially outward such that each respective implant firmly contacts the opposing faces of the interior wall of the respective cortical bone.

12. The method of claim 7, wherein the first and second implants each comprise at least one extrusion bore extending through a distal end portion of the respective implant and intersecting the respective internal bore, and wherein the method further comprises injecting a bone filler into the respective internal bore of each implant such that the bone filler is extruded from the respective extrusion bore and disposed within a costal margin end portion of the respective cortical bone.

13. The method of claim 7, wherein opposing distal ends of the fixation pin comprise threads, and wherein pulling the first and second halves of the severed sternum together comprises:
pulling the first and second halves together such that the opposing first and second distal ends of the fixation pin is pushed into contact with a costal margin face of the interior wall; and turning the fixation pin such that each threaded distal end of the fixation pin is threaded into the costal margin of the respective half of the severed sternum.

14. The method of claim 7, wherein the fixation pin comprises an internal lumen, and wherein securing the first and second halves of the severed sternum together such that lateral separation of the first and second halves is prevented comprises:
  inserting a tie wire though the respective costal margins and through the fixation pin internal lumen; and
  twisting ends of the tie wire together to bring and hold the first and second severance faces into contact with each other and join the first and second halves of the severed sternum.

* * * * *